United States Patent
Hu et al.

(10) Patent No.: US 11,565,990 B2
(45) Date of Patent: Jan. 31, 2023

(54) PREPARATION OF 4-BROMO-2-(4'-ETHOXYPHENYL)-1-CHLOROBENZENE

(71) Applicant: WISDOM PHARMACEUTICAL CO., LTD, Nantong (CN)

(72) Inventors: Lin Hu, Nantong (CN); Tao Xu, Nantong (CN); Xiaolong Qiu, Nantong (CN); Xiaoyue Li, Nantong (CN); Zhiwei Zuo, Nantong (CN); Wenbo Liu, Nantong (CN); Lingling Chu, Nantong (CN); Ximeng Yuan, Nantong (CN); Ping Zou, Nantong (CN)

(73) Assignee: WISDOM PHARMACEUTICAL CO., LTD, Nantong (CN)

( * ) Notice: Subject to any disclaimer, the term of this patent is extended or adjusted under 35 U.S.C. 154(b) by 0 days.

(21) Appl. No.: 17/434,015

(22) PCT Filed: Jun. 9, 2021

(86) PCT No.: PCT/CN2021/099079
§ 371 (c)(1),
(2) Date: Aug. 26, 2021

(87) PCT Pub. No.: WO2022/116507
PCT Pub. Date: Jun. 9, 2022

(65) Prior Publication Data
US 2022/0267238 A1   Aug. 25, 2022

(30) Foreign Application Priority Data
Dec. 4, 2020 (CN) .......................... 202011400070.8

(51) Int. Cl.
*C07C 41/18* (2006.01)
(52) U.S. Cl.
CPC ................................... *C07C 41/18* (2013.01)
(58) Field of Classification Search
CPC .......... C07C 41/30; C07C 41/18; C07C 45/46
See application file for complete search history.

(56) References Cited

U.S. PATENT DOCUMENTS

2004/0138439 A1   7/2004   Deshpande et al.

FOREIGN PATENT DOCUMENTS

| CN | 103896752 A | | 7/2014 | |
|---|---|---|---|---|
| CN | 105061373 A | * | 11/2015 | |
| CN | 105061373 A | | 11/2015 | |
| CN | 107382679 A | | 11/2017 | |
| CN | 107540648 A | | 1/2018 | |
| CN | 107573311 A | | 1/2018 | |
| CN | 108084130 A | | 5/2018 | |
| CN | 110396040 A | | 11/2019 | |
| CN | 111662166 A | | 9/2020 | |
| CN | 112500267 A | | 3/2021 | |
| IN | 2010CH03942 | * | 10/2012 | |
| WO | 2010022313 A2 | | 2/2010 | |
| WO | WO-2010048358 A2 | * | 4/2010 | ........... A61K 31/155 |
| WO | WO-2015063726 A1 | * | 5/2015 | ............ C07C 41/30 |
| WO | 2015132803 A2 | | 9/2015 | |

OTHER PUBLICATIONS

Yang Qingxin, et al., New Method for the Synthesis of 3-aryl-2,5-Dihydrofurans, Technology & Experiment, 2013, pp. 21-24, vol. 27 No. 4.

* cited by examiner

*Primary Examiner* — Rosalynd A Keys
(74) *Attorney, Agent, or Firm* — Bayramoglu Law Offices LLC

(57) ABSTRACT

A more environmentally friendly synthesis method of 4-bromo-2-(4'-ethoxyphenyl)-1-chlorobenzene with simplified steps provides a more effective synthetic strategy for producing key intermediates of SGLT-2 inhibitors such as dapagliflozin, sotagliflozin, and ertugliflozin. In the presence of trifluoroacetic anhydride, 5-bromo-2-chlorobenzoic acid and phenetole are selected to complete a direct acylation reaction under the catalysis of boron trifluoride diethyl etherate, and triethylsilane is added thereinto without treatment for one-pot reaction to obtain a target compound 4-bromo-2-(4'-ethoxyphenyl)-1-chlorobenzene.

6 Claims, No Drawings

PREPARATION OF 4-BROMO-2-(4'-ETHOXYPHENYL)-1-CHLOROBENZENE

CROSS REFERENCE TO THE RELATED APPLICATIONS

This application is the national phase entry of International Application No. PCT/CN2021/099079, filed on Jun. 9, 2021, which is based upon and claims priority to Chinese Patent Application No. 202011400070.8, filed on Dec. 4, 2020, the entire contents of which are incorporated herein by reference.

TECHNICAL FIELD

The present disclosure belongs to the field of synthesis methods of compounds, and particularly relates to a synthesis method of compound 4-bromo-2-(4'-ethoxyphenyl)-1-chlorobenzene.

BACKGROUND

SGLT-2 protein is present in the lumen of the human glomerular epithelial cell. In the presence of the SGLT-2 protein, 90% of glucose filtrated by renal tubules is reabsorbed. Hence, the blood glucose can go down provided that the biological action of the SGLT-2 protein is inhibited. The unique hypoglycemic mechanism of SGLT-2 inhibitors, as novel hypoglycemic agents, is not related to insulin, and the SGLT-2 inhibitors are new targets of insulin-independent anti-hyperglycemic agents, which pose a very low risk of hypoglycemia. Compared with other anti-hyperglycemic agents, the SGLT-2 inhibitors have a novel mechanism of action, opening up a new route to the excretion of excess glucose from the blood. The SGLT-2 inhibitors have excellent effects on hyperglycemia therapy, cardiovascular protection, and renal protection, and may even be used for cancer therapy in combination with ascorbic acid and quinones.

At present, a plurality of SGLT-2 inhibitors are under development in China, e.g., henagliflozin (Jiangsu Hengrui Medicine Co., Ltd.), rongliflozin (Sunshine Lake Pharma Co., Ltd.), and galigliflozin (Xuanzhu Biopharmaceutical Co., Ltd.). There are dapagliflozin, canagliflozin, empagliflozin, ertugliflozin, luseogliflozin, ipragliflozin, tofogliflozin, and sotagliflozin which have been on the market around the world. Their chemical structural formulas are shown as follows:

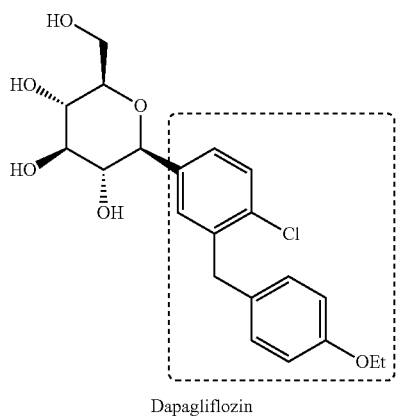

Dapagliflozin

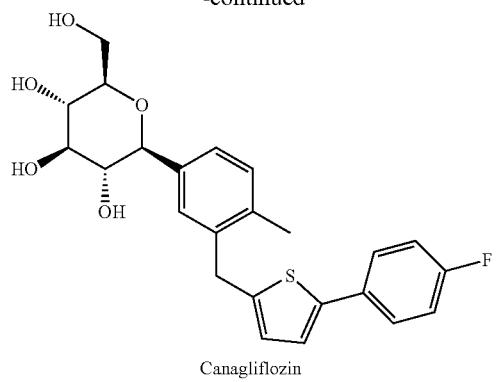

Canagliflozin

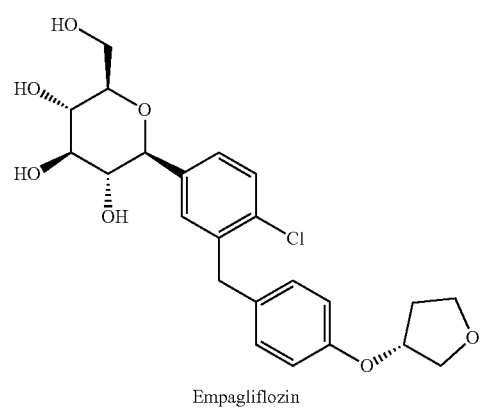

Empagliflozin

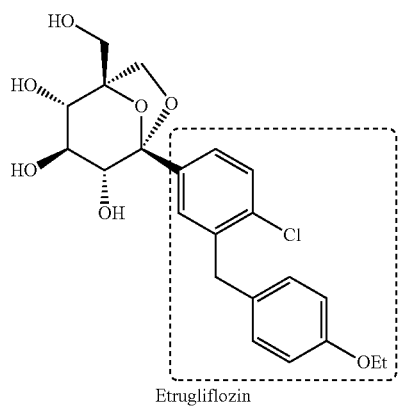

Etrugliflozin

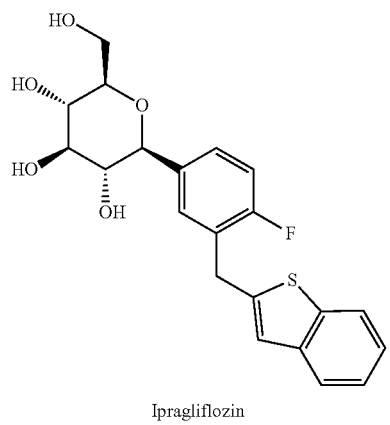

Ipragliflozin

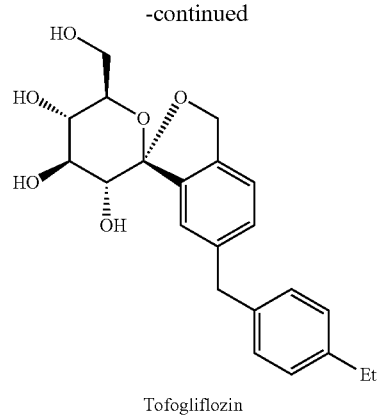

Tofogliflozin

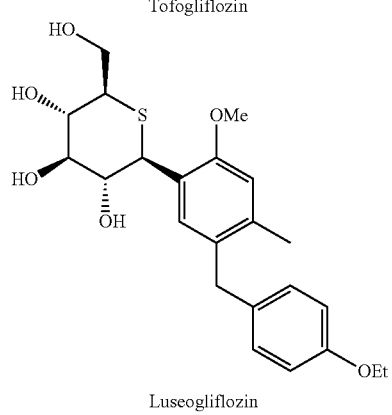

Luseogliflozin

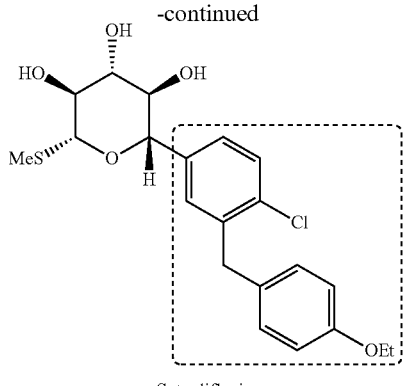

Sotagliflozin

It can be seen above, that these SGLT-2 inhibitors have a similar chemical structure, all of which include a similar glycosyl group (a six-membered heterocycle, mainly tetrahydropyran ring) attached to aryl groups. Among them, dapagliflozin, ertugliflozin, and sotagliflozin have the same aryl group, and compound 4-bromo-2-(4'-ethoxyphenyl)-1-chlorobenzene is a common key intermediate. For example, the US patent No. US2004138439 disclosed a method for synthesizing dapagliflozin from the compound as follows:

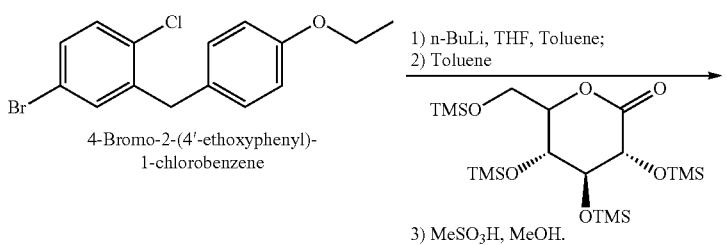

4-Bromo-2-(4'-ethoxyphenyl)-1-chlorobenzene

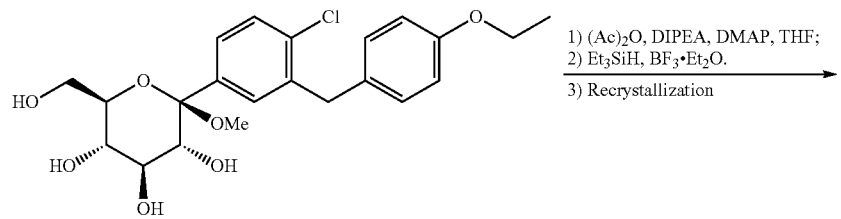

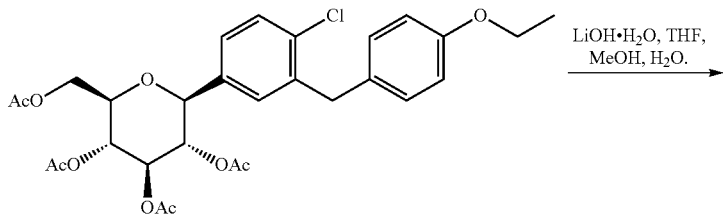

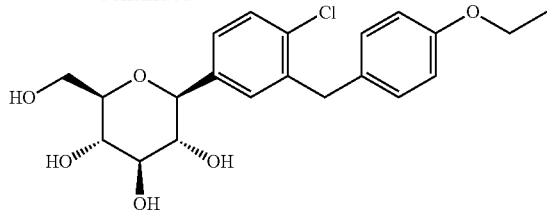

Dapagliflozin

A synthesis methods of the compound 4-bromo-2-(4'-ethoxyphenyl)-1-chlorobenzene is reported in the US patent No. US2004138439, the PCT applications No. WO2010/22313A2, and No. WO2015/132803 A2, wherein 5-bromo-2-chlorobenzoic acid is used as an initiator; after acyl chlorination, the initiator is subjected to a Friedel-Crafts acylation with phenetole under the catalysis of aluminum chloride, and then the resulting reaction product is purified and separated to obtain a diaryl ketone compound; the diaryl ketone compound is reduced to obtain 4-bromo-2-(4'-ethoxyphenyl)-1-chlorobenzene.

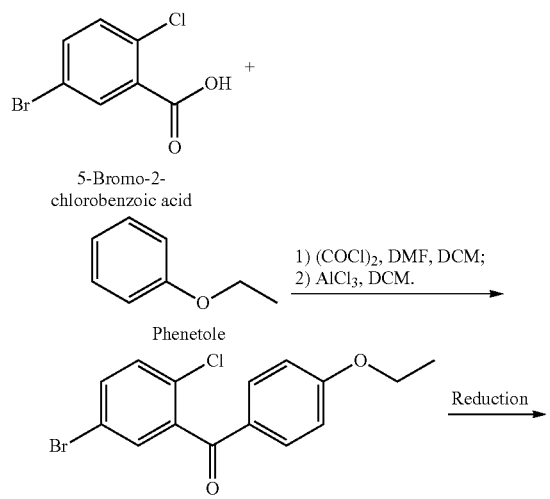

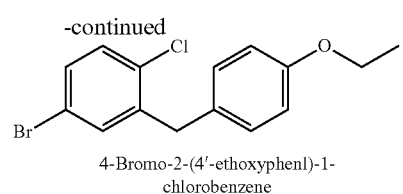

4-Bromo-2-(4'-ethoxyphenl)-1-chlorobenzene

The method has the advantages of short steps, excellent selectivity, and high yield, and the disadvantages of the use of a plurality of acid acylating chlorination reagents and the production of acidic waste in the acylation, and the use of aluminum chloride and acidic wastewater problems in the Friedel-Crafts reaction, which do not meet the green production demand and substantially increase the corrosion resistance requirement and maintenance costs of the production equipment.

Other methods reported in the Chinese Patents No. CN107382679 A, CN107573311A, CN107540648A, and CN108084130A are based on the Friedel-Crafts alkylation. These methods have longer steps, and utilize the Friedel-Crafts alkylation involved by benzyl alcohols or benzyl halides to construct diarylmethane through. Further, due to the presence of halogenation and Sandmeyer reaction, there are selection problems of alkylation reaction, and some safety problems, so the alkylation reaction is less efficient and convenient than acylation reaction.

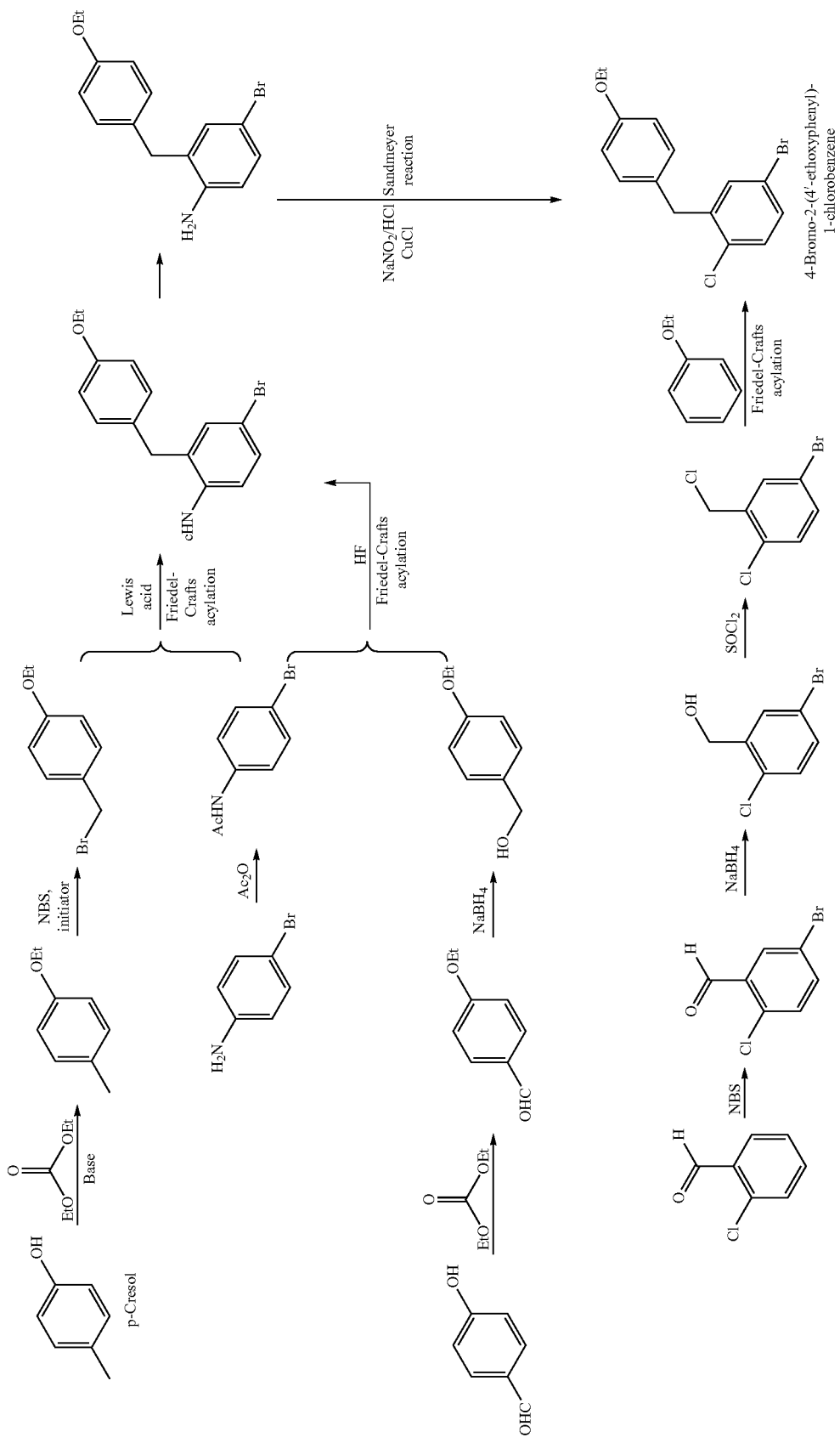

Therefore, the existing acylation methods for synthesizing 4-bromo-2-(4'-ethoxyphenyl)-1-chlorobenzene have the problems of the use of acidic materials and the production of acid waste gas (hydrogen chloride, and the like) and acidic wastewater (aluminum chloride, and the like). The alkylation methods have the problems of long steps, poor selectivity, and safe reaction, which are huge troubles in large-scale industrial production.

As described, SGLT-2 inhibitor, as anti-hyperglycemic agents, have a broad market prospect. Empagliflozin and dapagliflozin have been best-selling drug varieties with an annual sales of more than 1 billion USD; it is necessary to further develop an efficient and environmentally friendly synthesis method of 4-bromo-2-(4'-ethoxyphenyl)-1-chlorobenzene as a common key intermediate for dapagliflozin, ertugliflozin, and sotagliflozin.

SUMMARY

An objective of the present disclosure is to provide a more environmentally friendly synthesis method of 4-bromo-2-(4'-ethoxyphenyl)-1-chlorobenzene with simplified steps, which is used in the industrial production of some SGLT-2 inhibitor hypoglycemic agents. A synthetic route of the present disclosure is as follows:

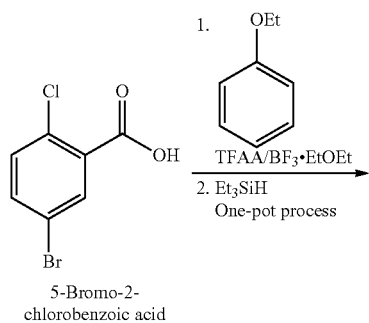

5-Bromo-2-chlorobenzoic acid

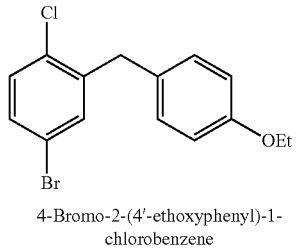

4-Bromo-2-(4'-ethoxyphenyl)-1-chlorobenzene

After 5-bromo-2-chlorobenzoic acid as an initiator reacts with phenetole in the presence of trifluoroacetic anhydride (TFAA) and a catalytic amount of boron trifluoride diethyl etherate (BF$_3$.EtOEt), triethylsilane is directly added thereinto without treatment for one-pot reaction to obtain a target compound 4-bromo-2-(4'-ethoxyphenyl)-1-chlorobenzene. The method is conducted under mild conditions in a simple and efficient manner, does not use acylating chlorination reagents and aluminum chloride, and completes the acylation and the carbonyl reduction in one pot only using a catalytic amount of boron trifluoride diethyl etherate and trifluoroacetic acid concomitant in the reaction as acid catalysts. Compared with conventional synthesis methods, aftertreatment is easy; the target compound can be obtained after simple washing, concentration, and crystallization; meanwhile, the method does not involve the disposal of unmanageable waste such as a mass of acid gases and acidic aluminum chloride wastewater, is green and environmentally friendly, has excellent practicability, and is suitable for use in large-scale industrial production.

DETAILED DESCRIPTION OF THE EMBODIMENTS

The present disclosure can be more specifically understood from the following example, but the following example is exemplary and does not limit the scope of the present disclosure. All simple substitutions and improvements of the present disclosure made by those skilled in the art are included in the technical solution claimed by the present disclosure.

Example 1: Synthesis of 4-bromo-2-(4'-ethoxyphenyl)-1-chlorobenzene

TFAA (84.0 g, 400 mmol), phenetole (14.7 g, 120 mmol), and boron trifluoride diethyl etherate (1.42 g, 10 mmol) were successively added into a 250 mL four-neck flask, 5-bromo-2-chlorobenzoic acid (23.5 g, 100 mmol) was introduced in portions, and a mixture was heated to 30±5° C. under stirring and held for reaction for 6 h to obtain a dark brown solution. After cooling to room temperature, triethylsilane (34.9 g, 300 mmol) was added into the mixture; the mixture was reheated to 55-60° C. and held for reaction for 18 h. After cooling, low boiling-point solvent was removed by vacuum concentration; residues were washed with dichloromethane (150 mL) and saturated sodium bicarbonate solution (60 mL) and separated; the organic layer was collected, washed with water (60 mL×2) twice, and concentrated. Residues were recrystallized with ethanol, filtered, and blow-dried at 40° C. to obtain a white target compound (24.3 g, yield 74.5%).

What is claimed is:
1. A method of synthesizing 4-bromo-2-(4'-ethoxyphenyl)-1-chlorobenzene in one pot, consisting of:
preparing the 4-bromo-2-(4'-ethoxyphenyl)-1-chlorobenzene by the following reaction formula:

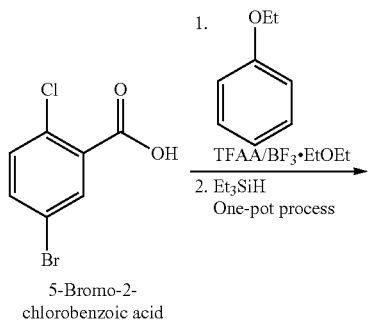

5-Bromo-2-chlorobenzoic acid

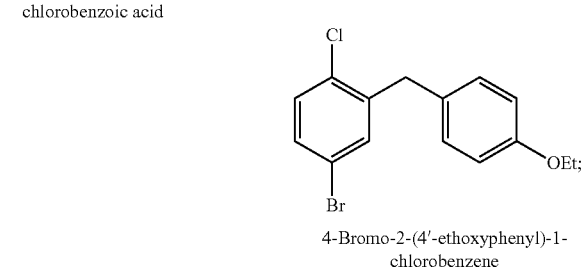

4-Bromo-2-(4'-ethoxyphenyl)-1-chlorobenzene wherein 5-bromo-2-chlorobenzoic acid is heated to a first temperature and held for reaction with phenetole in the presence of trifluoroacetic anhydride (TFAA) and a catalytic amount of boron trifluoride diethyl etherate ($BF_3.EtOEt$) to obtain a first mixture, after the first mixture is cooled to room temperature, the triethylsilane is directly added to the first mixture in the pot to obtain a second mixture, the second mixture is heated to a second temperature and held for reaction to obtain the 4-bromo-2-(4'-ethoxyphenyl)-1-chlorobenzene.

2. The method according to claim 1, wherein the first mixture is heated to a first temperature of from 25° C. to 35° C.

3. The method according to claim 2, wherein the first mixture is held in the first temperature for 6 h.

4. The method according to claim 1, the second mixture is heated to a second temperature of from 55° C. to 60° C.

5. The method according to claim 4, wherein the second mixture is held in the second temperature for 18 h to obtain the 4-bromo-2-(4'-ethoxyphenyl)-1-chlorobenzene.

6. The method according to claim 1, wherein a molar amount of the boron trifluoride diethyl etherate is one tenth of a molar amount of the 5-bromo-2-chlorobenzoic acid.

\* \* \* \* \*